United States Patent
Cosmescu

(10) Patent No.: US 9,925,007 B2
(45) Date of Patent: Mar. 27, 2018

(54) SMOKE EVACUATION ATTACHMENT DEVICE FOR LASER RESURFACING HANDPIECE

(71) Applicant: I.C. Medical, Inc., Phoenix, AZ (US)

(72) Inventor: Ioan Cosmescu, Phoenix, AZ (US)

(73) Assignee: I.C. Medical, Inc., Phoenix, AZ (US)

( * ) Notice: Subject to any disclaimer, the term of this patent is extended or adjusted under 35 U.S.C. 154(b) by 3 days.

(21) Appl. No.: 14/199,920

(22) Filed: Mar. 6, 2014

(65) Prior Publication Data

US 2014/0257260 A1   Sep. 11, 2014

Related U.S. Application Data

(60) Provisional application No. 61/773,256, filed on Mar. 6, 2013.

(51) Int. Cl.
*A61B 18/20* (2006.01)

(52) U.S. Cl.
CPC ...... *A61B 18/203* (2013.01); *A61B 2018/202* (2013.01)

(58) Field of Classification Search
CPC ............ A61B 18/203; A61B 2018/202; A61B 2218/008
USPC .......................................................... 606/41
See application file for complete search history.

(56) References Cited

U.S. PATENT DOCUMENTS

| | | | | |
|---|---|---|---|---|
| 5,693,044 A | * | 12/1997 | Cosmescu | A61B 18/042 604/35 |
| 6,117,134 A | * | 9/2000 | Cunningham et al. | A61B 18/1402 604/35 |
| 6,146,353 A | * | 11/2000 | Platt, Jr. | A61B 18/00 604/22 |
| 2012/0203223 A1 | * | 8/2012 | Terry | A61B 18/1402 606/42 |

\* cited by examiner

*Primary Examiner* — Michael Carey
(74) *Attorney, Agent, or Firm* — Zeman-Mullen & Ford, LLP

(57) ABSTRACT

A smoke evacuation attachment device for attachment to a laser resurfacing handpiece that includes a channel for evacuating smoke, dead skin cells, and other debris from the application site of the laser and which has a low profile to preclude encumbering the use of the laser handpiece.

18 Claims, 2 Drawing Sheets

SMOKE EVACUATION ATTACHMENT DEVICE FOR LASER RESURFACING HANDPIECE

CROSS-REFERENCE TO RELATED APPLICATIONS

This application claims priority to provisional patent application having Ser. No. 61/773,256, filed Mar. 6, 2013, which is herein incorporated by reference in its entirety.

FIELD OF INVENTION

The present invention generally relates to a smoke evacuation attachment device for a laser resurfacing handpiece. More particularly, the present invention relates to a smoke evacuation attachment device that comprises a very low profile thereby enabling the user of the laser resurfacing handpiece to efficiently remove smoke, dead skin cells, and other debris from the site of application without encumbering the user of the handpiece from effectively and efficiently applying the handpiece to the patient/client for skin resurfacing.

BACKGROUND OF THE INVENTION

Laser resurfacing of the skin has become extremely popular to reduce skin irregularities such as blemishes and acne scars and also to reduce wrinkles Laser resurfacing involves directing short, concentrated pulsating beams of light at the skins surface to be treated.

Two common types of lasers used in laser resurfacing are carbon dioxide and erbium. Both vaporize skin cells damaged at the surface level. Skin resurfacing with carbon dioxide lasers involves the use of very short pulsed light energy or continuous light beams that are delivered in a scanning pattern to remove thin layers of skin with minimal heat damage. Skin resurfacing with an erbium laser can remove surface level and moderately deep lines and wrinkles with minimal burning of surrounding tissue.

Smoke, dead skin cells, and other debris can be produced at the application site when using lasers to resurface the skin because laser resurfacing of the skin involves removing thin layers of skin and vaporizing skin cells. Removal of smoke, debris, dead skin cells etc. from the application site of the laser enables the individual performing the laser resurfacing to better see the application site and to remove contaminants from the new surface of the skin exposed from the laser resurfacing application.

Accordingly, there is a need for a smoke evacuation attachment device that can be easily attached to a laser resurfacing handpiece to enable those employing the handpiece to quickly and easily remove smoke, dead skin cells, and other debris that is formed at the application site of the laser. In addition, there is a need for a smoke evacuation attachment device of a laser handpiece that has a very low profile thereby enabling the individual employing the handpiece to efficiently and effectively utilize the handpiece without any additional encumbrance.

SUMMARY OF THE INVENTION

The present invention is directed to a smoke evacuation attachment device for a laser resurfacing handpiece that includes a generally planar shaped member having a thickness with a channel contained therein that has first and second openings where the first opening is capable of being positioned near the part of a laser handpiece where skin resurfacing takes place (i.e. where the laser is emitted and applied to the skin) and the second opening is capable of being connected to a vacuum tube to which a vacuum can be applied, and at least one clip member attached to the generally shaped planar member that is capable of clipping onto a laser resurfacing handpiece so that it attaches and secures the generally planar shaped member to the laser handpiece. The clip member may be attached to the bottom and/or the side of the generally planar shaped member so that at least a portion of the laser handpiece is positioned below the channel when the smoke evacuation attachment device is attached to the laser handpiece.

The smoke evacuation attachment device may also include a hood element positioned over the first opening of the channel and, in one embodiment, the hood element may be contiguous with, and comprise at least a portion of, the top of the generally planar shaped member. Further, the first opening in the channel may be contained within the bottom of the generally planar shaped member such that the hood element is positioned over it.

The smoke evacuation attachment device may also include one or more ridge members that are positioned about the circumference of a tubular member which is formed around the second opening and at least a portion of the channel to assist in retaining the connection of a vacuum tube to the second opening. In one embodiment, the tubular member may be contiguous with, and comprise at least a portion of, the generally planar shaped member adjacent to the second opening.

At least a portion of the channel in the generally planar shaped member may have a circular shaped cross-section and/or at least a portion of the channel in the generally planar shaped member may have a rectangular shaped cross-section. Further, the generally planar shaped member may have a rectangular shaped portion and a square shaped portion where the channel is contained within both the rectangular and square shaped portions of the generally planar shaped member. In addition, a portion of the channel adjacent to the second opening may be located above at least a portion of the top of the generally planar shaped member.

Another exemplary embodiment of the smoke evacuation attachment device of the present invention includes a generally planar shaped member with a channel having first and second openings where at least a portion of the channel has a rectangular shaped cross-section and at least one clip member attached to the generally planar shaped member. In addition, at least a portion of the channel in the generally planar shaped member may have a circular cross-section.

The clip member may be attached to the bottom and/or the side of the generally planar shaped member so that at least a portion of the laser handpiece is positioned below the channel when the smoke evacuation attachment device is attached to the laser handpiece. The smoke evacuation attachment device may also include a hood element positioned over the first opening of the channel and, in one embodiment, the hood element may be contiguous with, and comprise at least a portion of, the top of the generally planar shaped member. Further, the first opening in the channel may be contained within the bottom of the generally planar shaped member such that the hood element is positioned over it.

This exemplary embodiment of the smoke evacuation attachment device may also include one or more ridge members that are positioned about the circumference of a tubular member which is formed around the second opening and at least a portion of the channel to assist in retaining the connection of a vacuum tube to the second opening. In one embodiment, the tubular member may be contiguous with, and comprise at least a portion of, the generally planar shaped member adjacent to the second opening. Further, the generally planar shaped member may have a rectangular shaped portion and a square shaped portion where the channel is contained within both the rectangular and square shaped portions of the generally planar shaped member. In addition, a portion of the channel adjacent to the second opening may be located above at least a portion of the top of the generally planar shaped member.

BRIEF DESCRIPTION OF THE DRAWINGS

The subject invention will hereinafter be described in conjunction with the appended drawing figures, wherein like numerals demote like elements.

DETAILED DESCRIPTION

Figure 1:
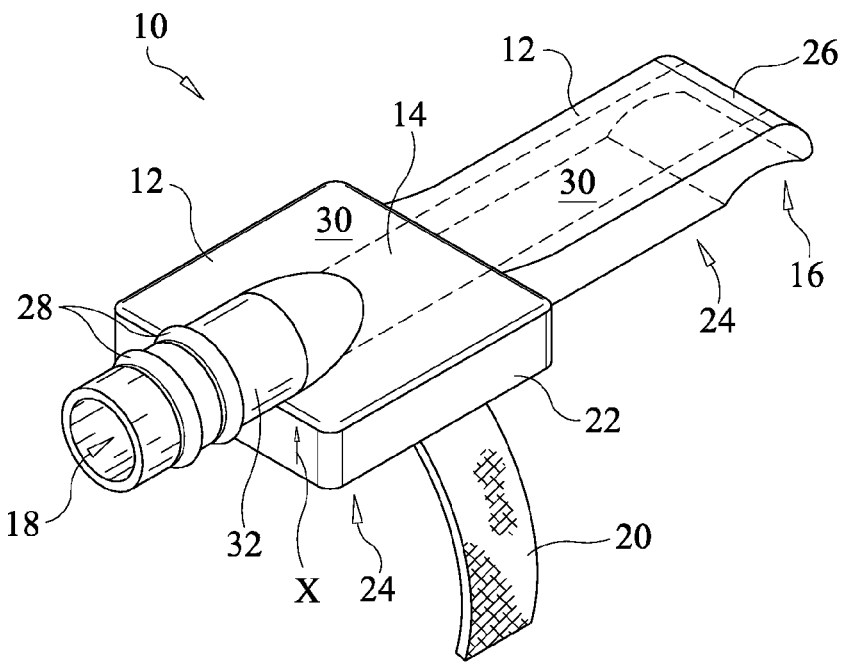
FIG. 1 is a perspective view of the smoke evacuation attachment device of the present invention.

The smoke evacuation attachment device of the present invention for attachment to a laser resurfacing handpiece has a low profile to preclude encumbering the use and operation of the laser handpiece and includes a channel for evacuating smoke, dead skin cells, and other debris from the application site of the laser. FIG. 1 is a perspective view of an exemplary embodiment of the smoke evacuation attachment device 10 of the present invention which includes a generally planar shaped member 12 having a thickness X and a channel 14 (shown in phantom) that has a first opening 16 capable of being positioned near a portion of a laser held handpiece where skin resurfacing occurs (i.e. where the laser is emitted and applied to the skin) and a second opening 18 that is capable of being connected to a vacuum tube to which a vacuum can be applied. Smoke evacuation attachment device also includes at least one clip member 20 attached to a side 22 and/or bottom 24 of generally planar shaped member 12 so that at least a portion of the laser handpiece is positioned below the channel 14 in the generally planar shaped member 12 when the smoke evacuation attachment device 10 is attached to the laser handpiece 100 (See FIG. 2).

Figure 2:
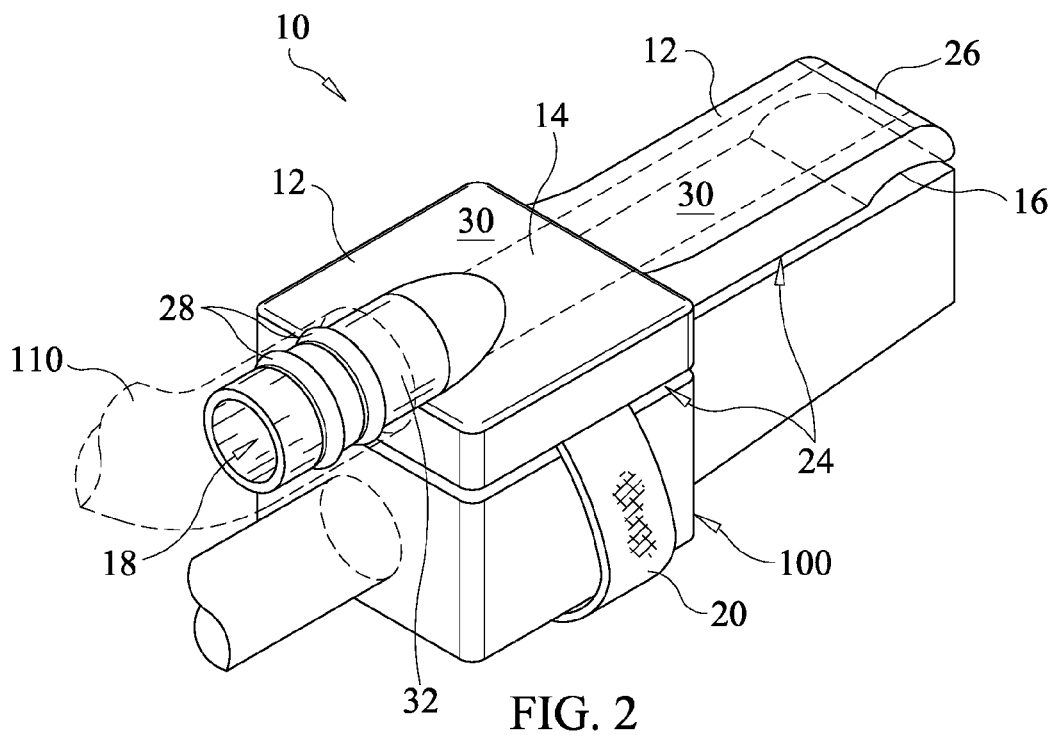
FIG. 2 is a perspective view of the smoke evacuation attachment device of the present invention shown attached to a laser resurfacing handpiece and also shows the smoke evacuation attachment device of the present invention connected to a vacuum tube.

FIG. 2 shows a perspective view of the smoke evacuation attachment device 10 of the present invention shown attached to a laser resurfacing handpiece 100 and also shows the smoke evacuation attachment device 10 of the present invention connected to a vacuum tube 110. The smoke evacuation attachment device 10 shown in FIGS. 1 and 2 also includes a hood element 26 positioned over first opening 16 of channel 14 and hood element 26 may be contiguous with, and comprised of, at least a portion of a top 30 of generally planar shaped member 12. First opening 16 of channel 14 is contained in the bottom 24 of generally planar shaped member 12.

Smoke evacuation attachment device 10 also includes one or more ridge members 28 that are positioned about the circumference of a tubular member 32 which is formed around second opening 18 and at least a portion of channel 14 to facilitate connection and retention of vacuum tube 110 to second opening 18. Tubular member 32 may be contiguous with, or comprised of, at least a portion of generally planar shaped member 12 that is adjacent to second opening 18.

Figure 3:
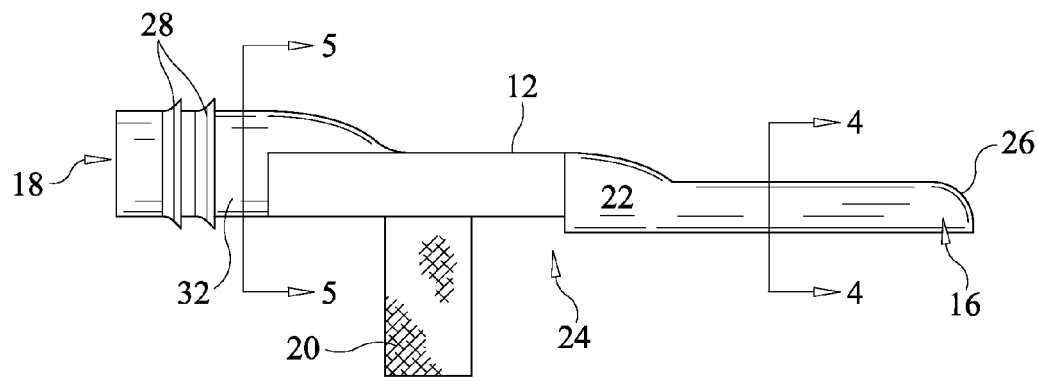
FIG. 3 is a side elevational view of the smoke evacuation attachment device of the present invention.
Figure 4:
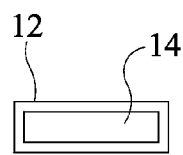
FIG. 4 is a cross-sectional view taken along line 4-4 of FIG. 3.
Figure 5:
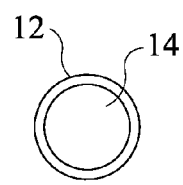
FIG. 5 is a cross-sectional view taken along line 5-5 of FIG. 3.

FIG. 3 is a side elevational view of the smoke evacuation attachment device 10 of the present invention. FIG. 4 is a cross-sectional view taken along line 4-4 of FIG. 3 and FIG. 5 is a cross-sectional view taken along line 5-5 of FIG. 3. As shown in FIGS. 4 and 5, a portion of channel 14 in generally planar shaped member 12 may have a rectangular shaped cross-sectional area and/or a circular shaped cross-sectional area. Channel 14 may comprise any number of configurations and shapes as long as generally planar shaped member 12 maintains a low profile in comparison to the shape of laser resurfacing handpiece 100. One exemplary configuration of channel 14 in generally planar shaped member 12 includes a rectangular shape near first opening 16 which extends into and through generally planar shaped member 12 past clip 20 and then transitions to a circular shape near second opening 18 and the area adjacent second opening 18.

Figure 6:
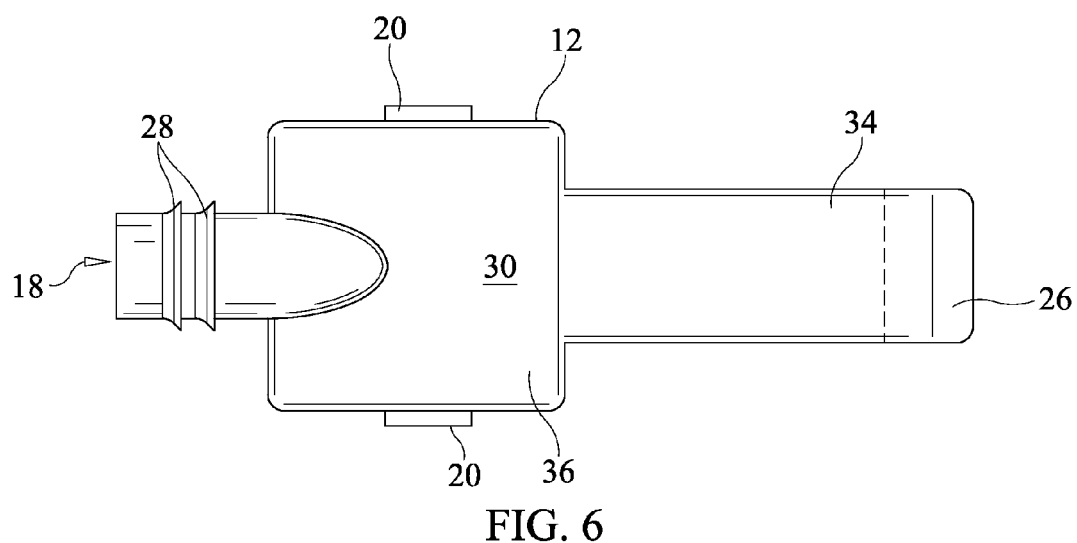
FIG. 6 is a top plan view of the smoke evacuation attachment device of the present invention.

A top plan view of smoke evacuation attachment device 10 of the present invention is shown in FIG. 6. As can be seen in FIG. 6, generally planar shaped member 12 may comprise a rectangular shaped portion 34 and a square portion 36 where the channel is contained within, and traverses, an interior of both the rectangular and square shaped portions 34, 36 of generally planar shaped member 12. Further, a portion of channel 14 contained within tubular member 32 adjacent to second opening 18 may be located above at least a portion of the top 30 of generally planar shaped member 12 as clearly shown in FIG. 3.

Still another exemplary embodiment of the smoke evacuation attachment device of the present invention may include, at a minimum, a generally planar shaped member with a channel contained in it having first and second openings where at least a portion of the channel has a rectangular shaped-cross section and a clip member attached to the generally planar shaped member. The rectangular shaped cross-section of the channel in the generally planar shaped member enables the smoke evacuation attachment device to exhibit and maintain a low profile in relation to the laser resurfacing handpiece and further aids in avoiding encumbrance of a user employing the laser resurfacing handpiece when it is attached to the smoke evacuation attachment device of the present invention.

The detailed description of exemplary embodiments of the invention herein shows various exemplary embodiments of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The invention claimed is:

1. A smoke evacuation attachment device for a laser resurfacing handpiece comprising:
    a generally planar shaped member having a thickness with a channel contained therein that has a first rectangular shaped opening capable of being positioned near a portion of the laser handpiece where skin resurfacing is taking place and a second opening capable of being connected to a vacuum tube;
    at least one clip member extending past a bottom of said generally planar shaped member; and
    a hood element positioned over the first rectangular shaped opening wherein the first rectangular shaped opening is a same width as the channel and the hood element is in horizontal alignment with the generally planar shaped member.

2. The smoke evacuation attachment device of claim 1 wherein the hood element comprises at least a portion of a top of said generally planar shaped member.

3. The smoke evacuation attachment device of claim 1 further comprising one or more ridge members positioned about the circumference of a tubular member which is formed around the second opening and at least a portion of the channel to assist in retaining connection of a vacuum tube to the second opening.

4. The smoke evacuation attachment device of claim 3 wherein the tubular member comprises a portion of the generally planar shaped member adjacent to the second opening.

5. The smoke evacuation attachment device of claim 1 wherein at least a portion of said channel has a circular shape.

6. The smoke evacuation attachment device of claim 1 wherein at least a portion of said channel has a rectangular shape.

7. The smoke evacuation attachment device of claim 1 wherein at least a portion of said channel has a circular shape and at least a portion of said channel has a rectangular shape.

8. The smoke evacuation attachment device of claim 1 wherein said generally planar shaped member comprises a rectangular shaped portion and a square shaped portion wherein said channel is contained within both the rectangular shaped portion and the square shaped portion.

9. The smoke evacuation attachment device of claim 1 wherein a portion of said channel adjacent to said second opening lies above at least a portion of a top of said generally planar shaped member.

10. A smoke evacuation attachment device for use with a laser resurfacing handpiece comprising:
    a generally planar shaped member with a channel contained therein having a first opening capable of being positioned near a portion of the laser resurfacing handpiece where laser resurfacing is taking place and a second opening capable of being connected to a vacuum tube wherein at least a portion of said channel has a rectangular shape and a portion of said channel adjacent to said second opening lies above at least a portion of a top of said generally planar shaped member;
    at least one clip member attached to a planar surface of said generally planar shaped member; and
    a hood element positioned over the first opening wherein the first opening is as wide as the channel.

11. The smoke evacuation attachment device of claim 10 wherein at least a portion of said channel has a circular shape.

12. The smoke evacuation attachment device of claim 10 wherein the clip member is attached to at least one of a bottom and a side of said generally planar shaped member such that at least a portion of a laser handpiece is positioned below said channel when the smoke evacuation attachment device is attached to the laser handpiece.

13. The smoke evacuation channel of claim 10 wherein the hood element comprises at least a portion of a top of said generally planar shaped member.

14. The smoke evacuation attachment device of claim 10 further comprising one or more ridge members positioned about the circumference of a tubular member which is formed around the second opening and at least a portion of the channel to assist in retaining connection of a vacuum tube to the second opening.

15. The smoke evacuation attachment device of claim 10 wherein said generally planar shaped member comprises a rectangular shaped portion and a square shaped portion wherein said channel is contained within both the rectangular shaped portion and the square shaped portion.

16. A smoke evacuation attachment device for use with a laser resurfacing handpiece comprising:
    a generally planar shaped member with a channel contained therein having first and second openings wherein said first opening has a rectangular shape that is as wide as the channel;
    at least one clip member extending east a bottom of said generally planar shaped member; and
    a hood element positioned over the first rectangular shaped opening.

17. A smoke evacuation attachment device for use with a laser resurfacing handpiece comprising a generally planar shaped member having a channel contained therein having a rectangular shaped opening that is a same width as the channel and a hood element positioned over the rectangular shaped opening.

18. The smoke evacuation attachment device of claim 17 further comprising at least one clip member extending past a bottom of said generally planar shaped member.

* * * * *